(12) United States Patent
Carrez et al.

(10) Patent No.: US 8,798,766 B2
(45) Date of Patent: Aug. 5, 2014

(54) NEUROSTIMULATION CATHETER

(75) Inventors: Jean-Luc Carrez, Ecouen (FR); Valéry Dalle, Gouvieux (FR); Pierrick Guyomarc'h, Ermont (FR); Claire Dulong, Rivecourt (FR); Cécile Gadenne, Rueil Malmaison (FR)

(73) Assignee: Vygon, Ecouen (FR)

( * ) Notice: Subject to any disclaimer, the term of this patent is extended or adjusted under 35 U.S.C. 154(b) by 1280 days.

(21) Appl. No.: 12/161,979

(22) PCT Filed: Jan. 15, 2007

(86) PCT No.: PCT/FR2007/000064
§ 371 (c)(1),
(2), (4) Date: Jul. 24, 2008

(87) PCT Pub. No.: WO2007/088256
PCT Pub. Date: Aug. 9, 2007

(65) Prior Publication Data
US 2009/0012578 A1   Jan. 8, 2009

(30) Foreign Application Priority Data

Feb. 2, 2006 (FR) ...................................... 06 00948

(51) Int. Cl.
*A61N 1/05* (2006.01)
*H01R 13/02* (2006.01)
(52) U.S. Cl.
CPC ............ *A61N 1/0551* (2013.01); *H01R 13/025* (2013.01); *H01R 2201/12* (2013.01)
USPC ........................................................ 607/116

(58) Field of Classification Search
CPC ..... A61N 1/375; A61N 1/3752; A61N 1/372; A61N 1/04; A61N 1/05; A61N 1/0529; A61N 1/0551; H01R 2201/12
USPC ........................ 607/115–118, 37–38; 439/909
See application file for complete search history.

(56) References Cited

U.S. PATENT DOCUMENTS

| | | | |
|---|---|---|---|
| 5,275,597 A * | 1/1994 | Higgins et al. | 606/33 |
| 5,372,603 A | 12/1994 | Acker et al. | |
| 5,599,295 A | 2/1997 | Rosen et al. | |
| 5,681,514 A * | 10/1997 | Woody | 264/104 |
| 6,134,476 A | 10/2000 | Arndt et al. | |
| 6,208,881 B1 * | 3/2001 | Champeau | 600/374 |
| 6,654,641 B1 * | 11/2003 | Froberg | 607/37 |

(Continued)

FOREIGN PATENT DOCUMENTS

EP   1605729 A   12/2005

*Primary Examiner* — Carl H Layno
*Assistant Examiner* — Jessica Anthony
(74) *Attorney, Agent, or Firm* — Levine Mandelbaum PLLC (57) ABSTRACT

The conductor is composed of at least one layer (2) of a material (A) that conducts electricity, said layer being applied to the outer face of the lateral wall of the tube (1) and being insulated by a non-conductive sheath (B) applied to the layer, In said conductive layer (2) forming, at the distal end of the tube, a distal ring (4) that matches the shape of the rounded distal end of N the tube and is not covered by the insulating sheath (B) of the layer, so as to form a neurostimulation contact, and said conductive layer (2) forming, at the proximal end of the tube, a proximal ring (3) that is not covered by the insulating sheath (B), so as to form an electrical connection.

18 Claims, 10 Drawing Sheets

(56) References Cited

U.S. PATENT DOCUMENTS

| | | | |
|---|---|---|---|
| 6,741,892 B1* | 5/2004 | Meadows et al. | 607/116 |
| 2004/0039434 A1 | 2/2004 | Schrom et al. | |
| 2004/0097965 A1* | 5/2004 | Gardeski et al. | 606/129 |
| 2005/0015130 A1* | 1/2005 | Gill | 607/116 |
| 2005/0150762 A1 | 7/2005 | Butters et al. | |
| 2005/0234522 A1* | 10/2005 | Ley et al. | 607/37 |

* cited by examiner

FIG_5

FIG_6

FIG_8

NEUROSTIMULATION CATHETER

The invention relates to a neurostimulation catheter formed by a flexible tube in a non-electrically conducting material, the distal end of which is rounded and which comprises an electric conductor which extends into the length of the tube for conducting an electric stimulation current from one end to the other end of the tube.

With neurostimulation, the practitioner may make sure that the catheter has reached the desired objective by the reaction of the plexus block to an electrical excitation from the distal end of the catheter.

In order to make a non-electrically conducting tube neurostimulable, it is known how to add to the tube an electric conductor which substantially extends along the length of the catheter between an electric contact connected with the conductor at the distal end of the tube for contact of the conductor with nerves or body tissues and an electric connector connected with the conductor at the proximal end of the tube for the electrical power supply of the conductor.

The conductor may be formed by a metal mandrel introduced into the lumen of the tube and which has to be removed after placing the tube in order to clear the lumen before putting the catheter into service, as described for example in publications GB 88 03 153, DE 1 807 487 and CA 2 260 080.

The conductor may also be permanently incorporated to the tube in order to allow stimulation at any moment, as described for example in publications DE 101 00976, U.S. Pat. No. 5,081,990.

Permanent incorporation of a metal conductor raises a problem of bulkiness if the conductor is placed inside the tube and complicates the making of the tube if the conductor is incorporated into the wall of the catheter.

The invention is aimed at avoiding these drawbacks.

This is achieved according to the invention by forming the conductor with at least one layer of an electrically conducting material applied on the outer face of the sidewall of the tube and insulated by a non-conducting cladding applied on the layer, said conducting layer forming at the distal end of the tube a distal ring which fits the rounded shape of the distal end of the tube and which is not covered by the insulating cladding of the layer so as to form a neurostimulation contact, and said conducting layer forming at the proximal end of the tube, a proximal ring which is not covered by the insulating cladding in order to achieve electrical connection.

In this way, the lumen of the tube remains totally clear and the making of the tube remains simple.

For example, an ink used for the silver drawing of electric tracks with a pen and a resistant acrylic cladding also applied with the pen are used; alternatively, an epoxy adhesive containing silver particles or a conducting ink without any binder which upon drying only leaves the metal, may be used. These examples are not exclusive of other choices.

Application is performed with the pen, or preferably by screen printing or pad printing.

The application of a conductive ink on the outer face of the wall of a catheter has already been proposed (WO/2005/060870) but essentially with the purpose of being able to apply an electrostatic method for accurately applying a drug onto the wall of the catheter.

Provision of a balloon catheter intended for a cardiovascular application, with two separate conductive layers for transmitting electrical power to an element associated with the balloon has also been proposed (U.S. Pat. No. 5,372,603).

In preferred embodiments, the catheter of the invention further has one or more of the following characteristics:

the conductive layer forms a line with calibrated width and thickness;

a split conducting tube is slipped onto the proximal end of the catheter in order to provide an electrical connection with the proximal ring;

the wall of the conducting tube is cut out longitudinally in order to form at least one elastic tab intended for providing electric contact between the tube and an electric wire held in contact with the tab;

the catheter is provided with a proximal base;

a connector is added onto the proximal end of the tube in order to hold the conducting wire;

said layer is formed by ink containing silver;

said layer is formed by a mixture of solvent and silver powder;

said layer was applied by screen printing, by pad printing or by an ink jet.

Exemplary embodiments of a catheter and base according to the invention will be described hereafter with reference to the appended figures wherein.

The catheter illustrated in the figures is formed by a flexible tube (1) in a non-electrically conducting material on the outer face of which was applied along a line (2) a layer (A) of an electrically conducting material which extends from the proximal end (1a) to the distal end (1b) of the tube (1) and which is locally clad with a layer of insulating material (B).

At its ends, the conductive layer forms two rings (3,4) of a few millimeters in length and the insulating cladding (B) has been interrupted before these rings.

One of the rings will be used as an electric power supply for the conductive cladding and the other ring will be used for transmitting the electric excitation to the nerves (plexus block) at the location where it is intended to stimulate or localize the nerves.

Between both rings, the human body must not be in contact with the conductor, whence the presence of an insulating cladding (based on plastic and solvent for example) on the conductive line, so that it is completely covered. In this way, both conductive rings are connected through an insulated conductor.

The distal conductive ring, as an electric contact, is a good solution for neurostimulation because it is not very bulky (thickness of 15-20 µm), and does not therefore generate any large overthickness which may interfere with the passage of the catheter into a needle; it allows the use of a catheter with an unblocked and unshrinked distal hole, which is better for the flow rate. This also avoids having to push strongly on the injection syringe.

If the catheter is blunt (rounded end) on the distal side, the ring may fit the rounded (atraumatic) shape.

The invention also relates to embodiments of a base to be mounted on the proximal end of a neurostimulation catheter, in particular of a catheter according to the invention, equipped with means for holding the catheter in the base and with means for providing an electric connection between an electric power supply conductor and the conductive cladding of the catheter, and capable of connecting the catheter to a device for supplying a solution, for example an injection syringe.

Figure 1:
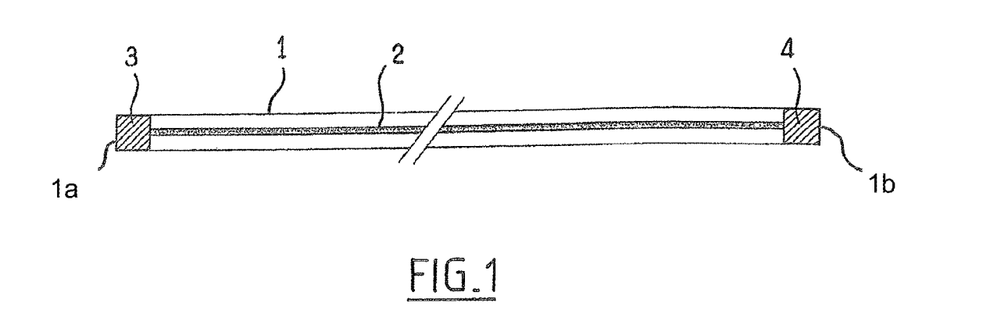
FIG. 1 is a block diagram of the catheter.
Figure 2:
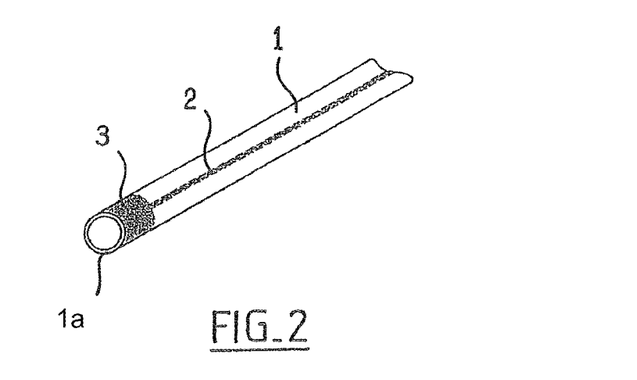
FIG. 2 is a perspective view of the proximal end of the catheter according to an embodiment.
Figure 3:
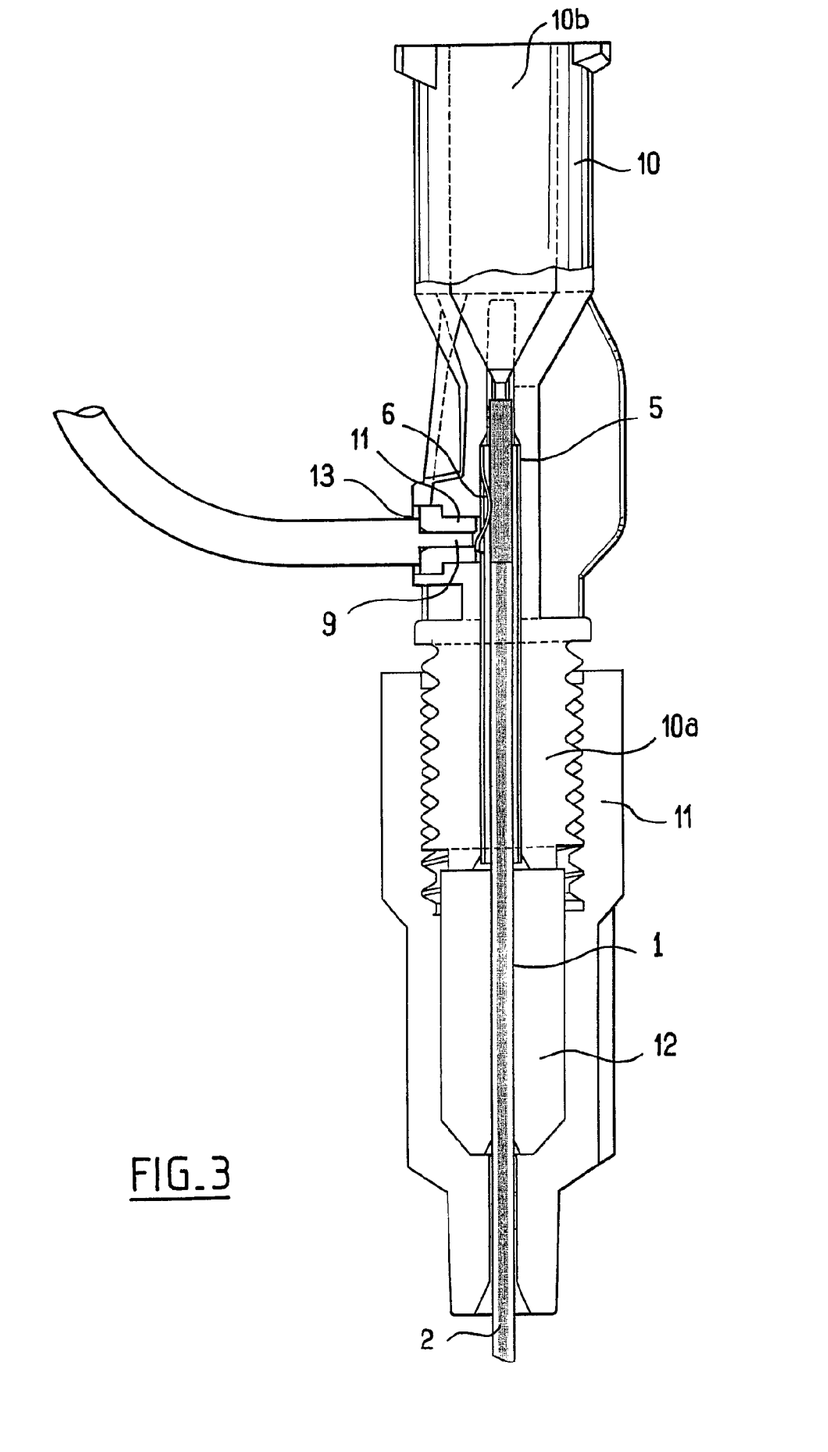
FIG. 3 is a longitudinal sectional view of an embodiment of a base for the catheter.
Figure 4:
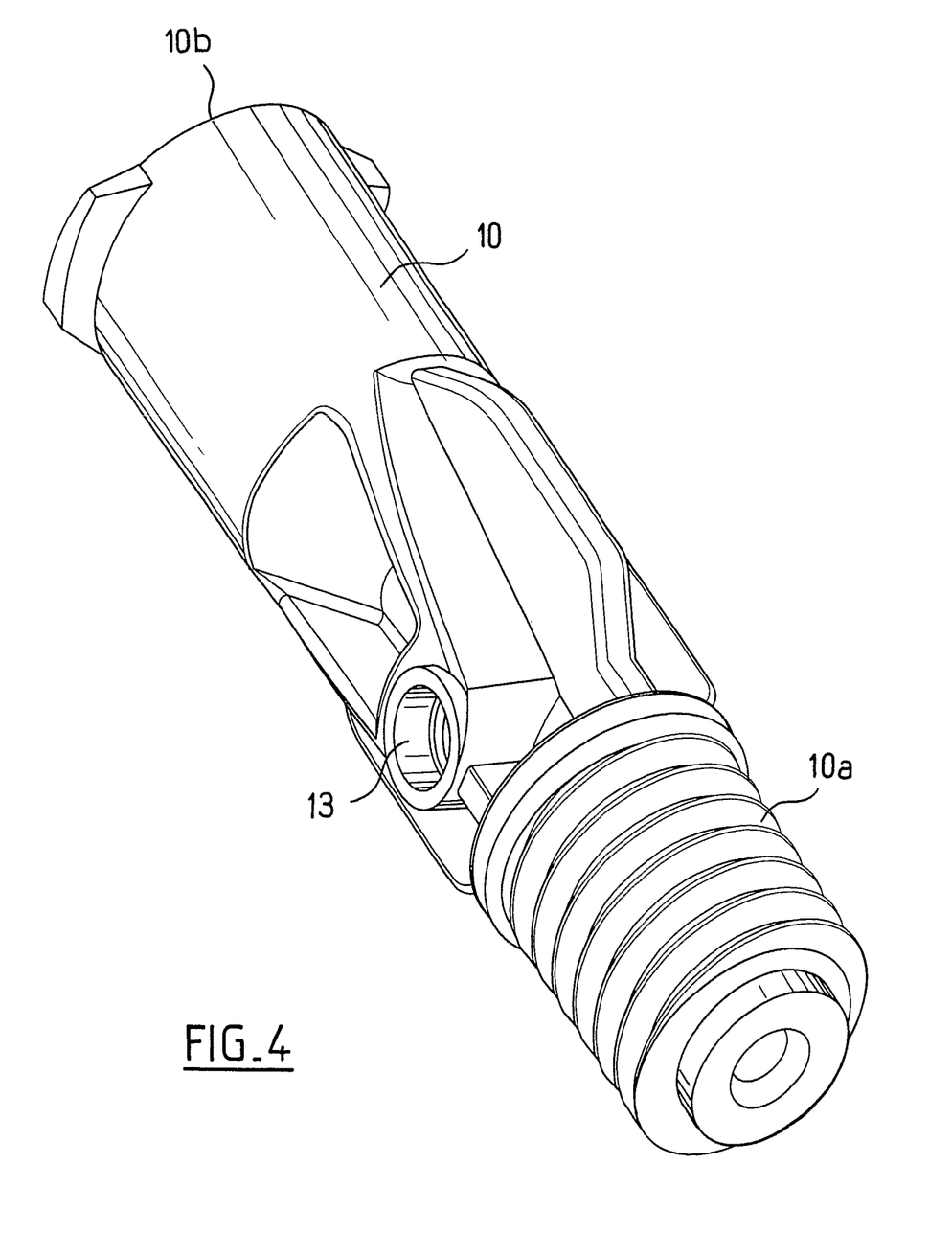
FIG. 4 is a perspective view of the tubular body of the base.
Figure 5:
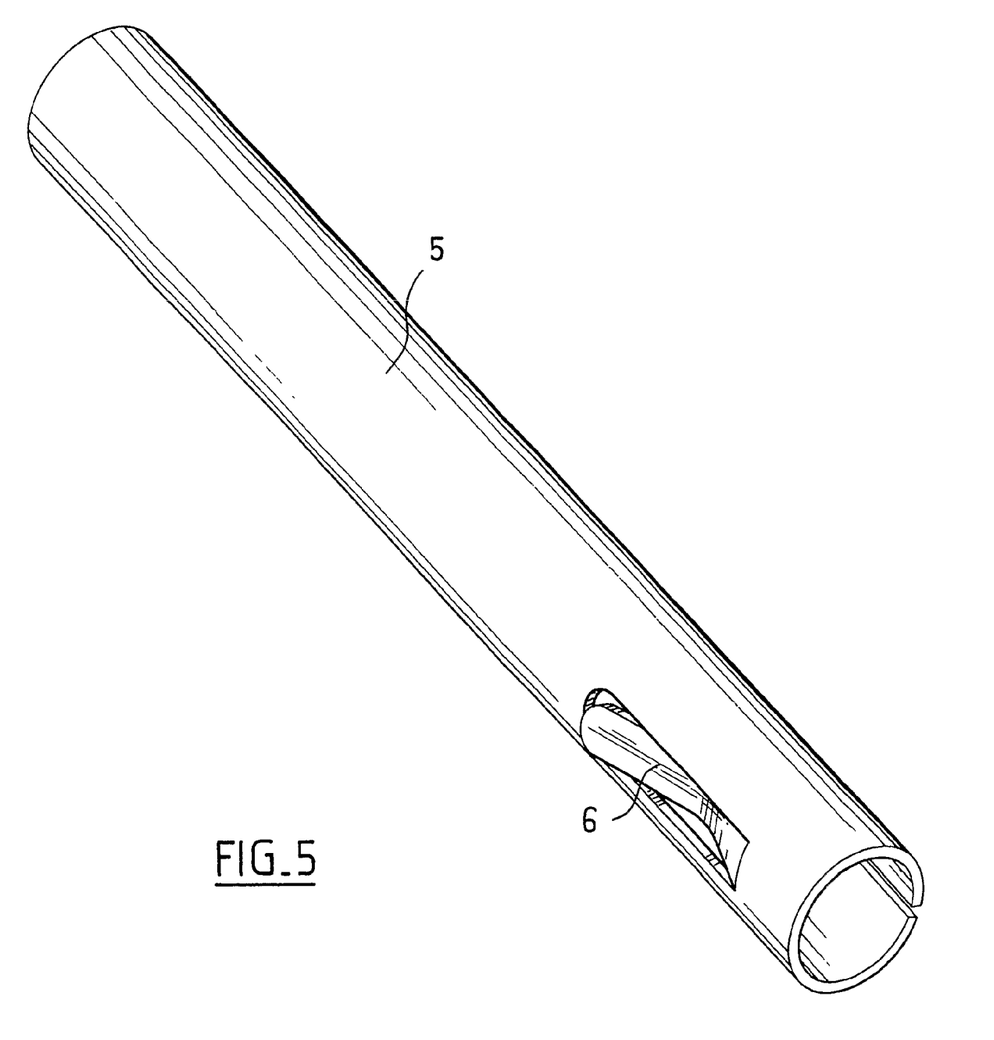
FIG. 5 is a detailed view of the conductive tube to be added onto the proximal end of the tubular portion of the catheter according to an embodiment of the invention.
Figure 6:
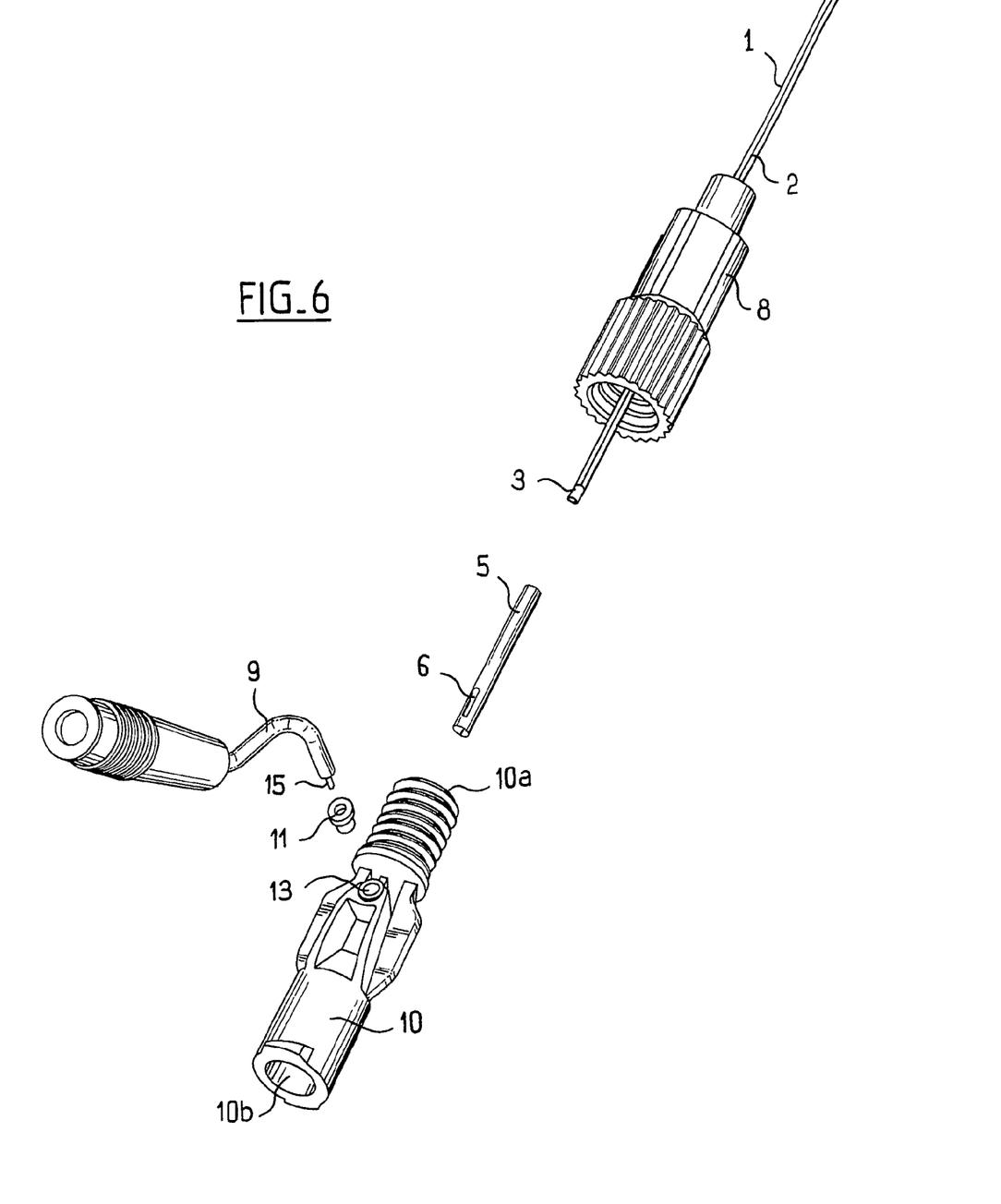
FIG. 6 is an exploded view.
Figure 7:
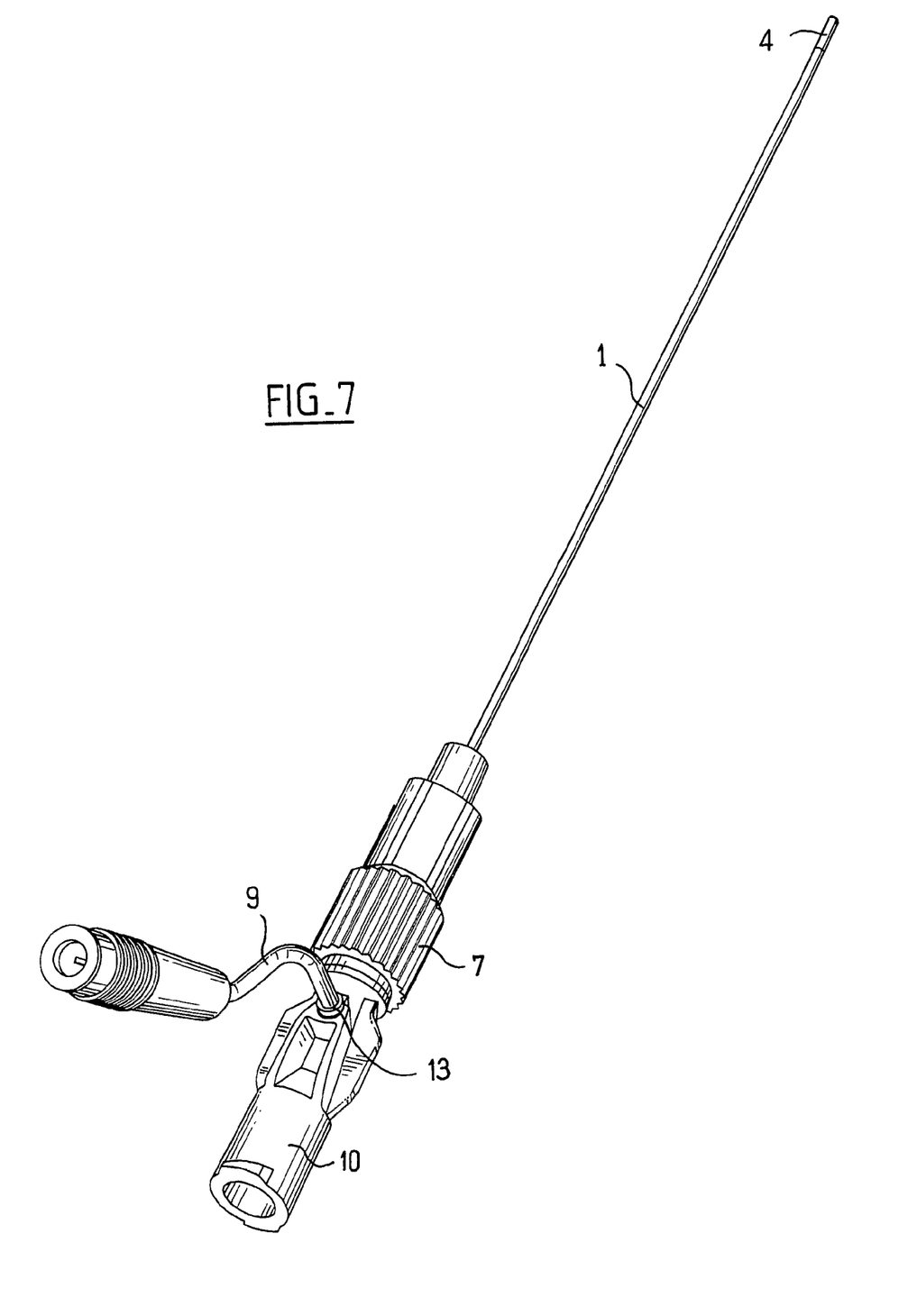
FIG. 7 is a perspective view of the catheter with its base, ready to be used.
Figure 8:
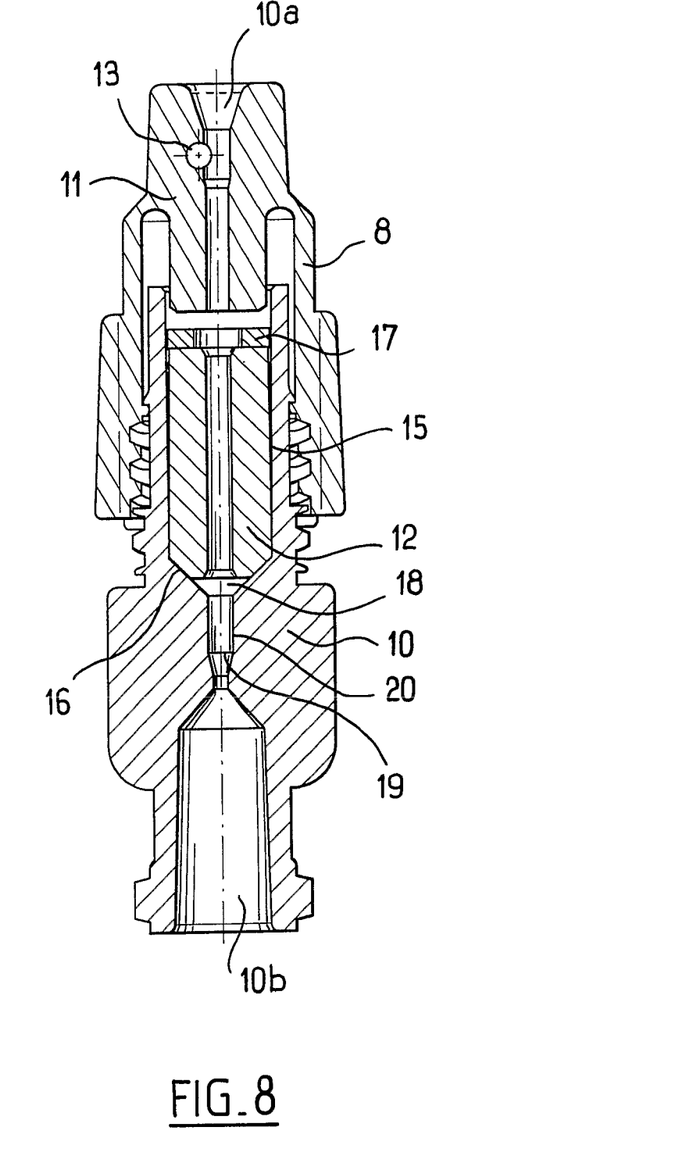
FIG. 8 is an axial sectional view of an alternative embodiment of the base of the catheter tube, before placing the catheter in the base and making electrical connection.
Figure 9:
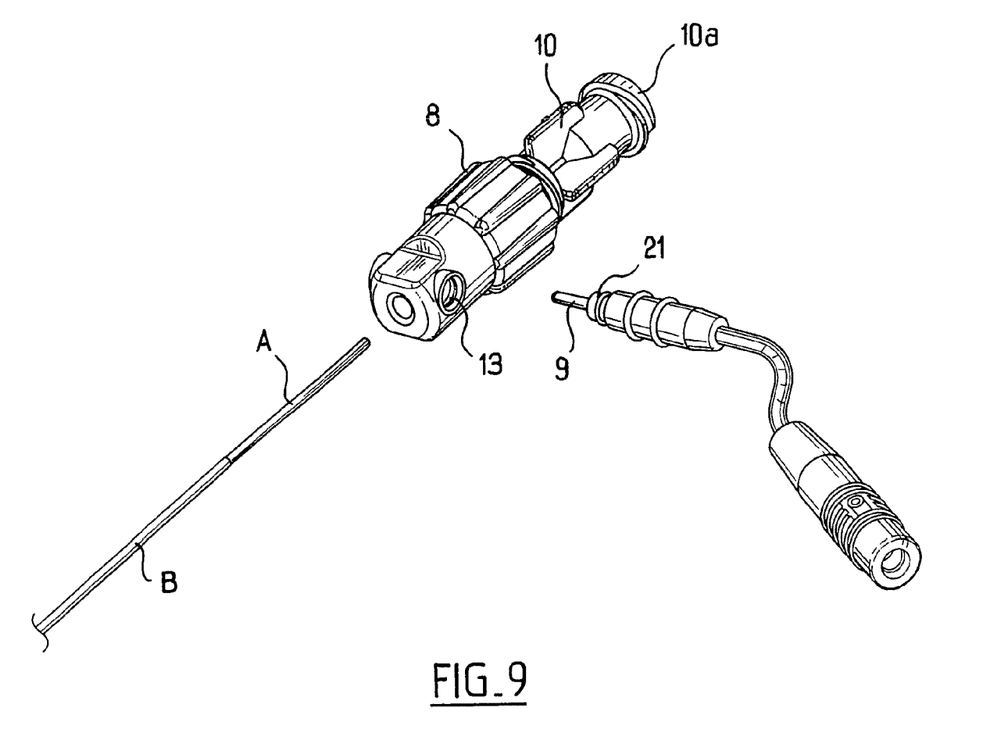
FIG. 9 is a perspective view of the base of FIG. 8.
Figure 10:
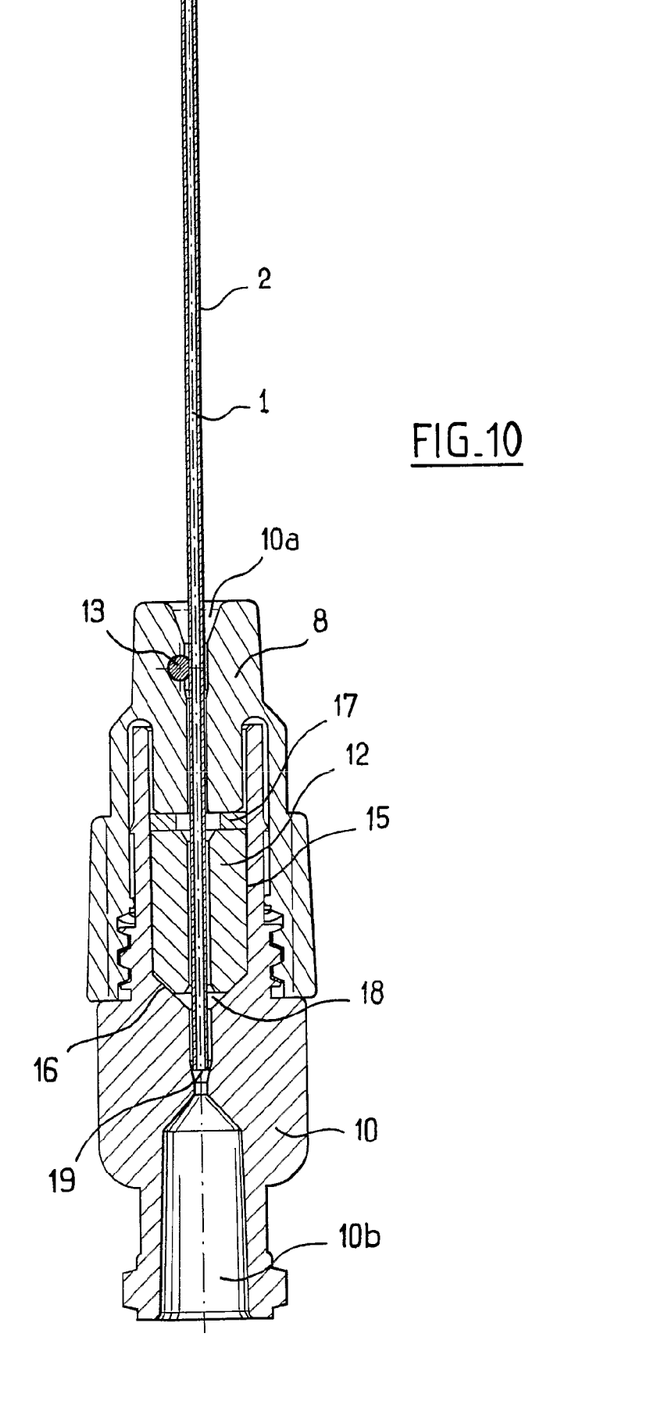
FIG. 10 shows the same section as that of FIG. 8 after placing the catheter in the base, tightening the nut and making electrical connection.
Figure 11:
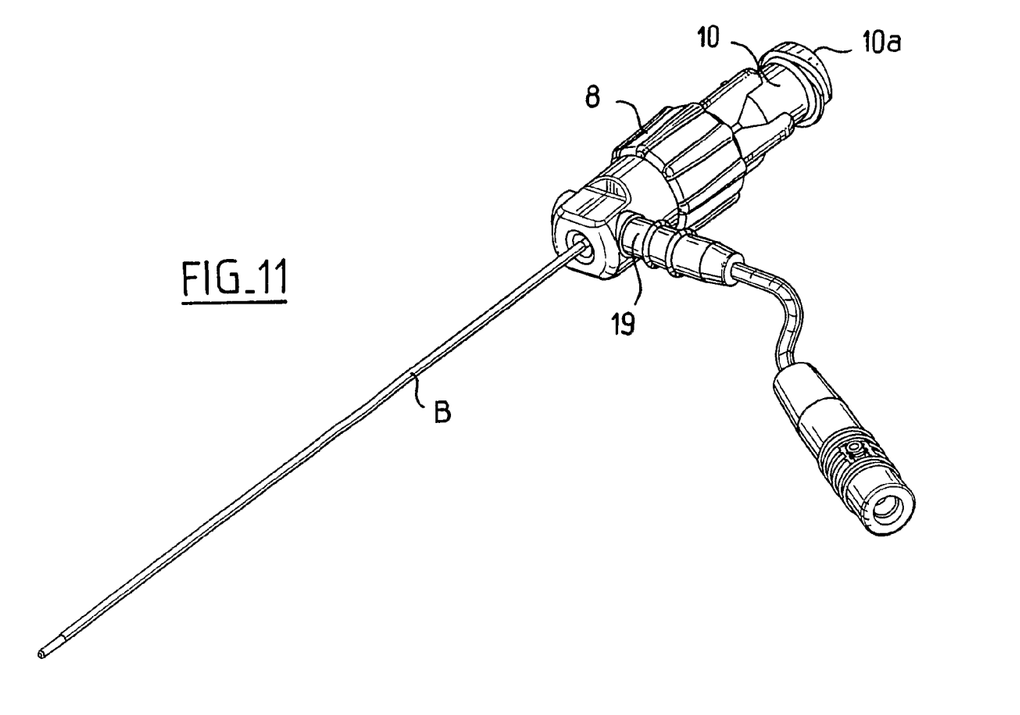
FIG. 11 is a perspective view of the base of FIG. 10.
Figure 12:
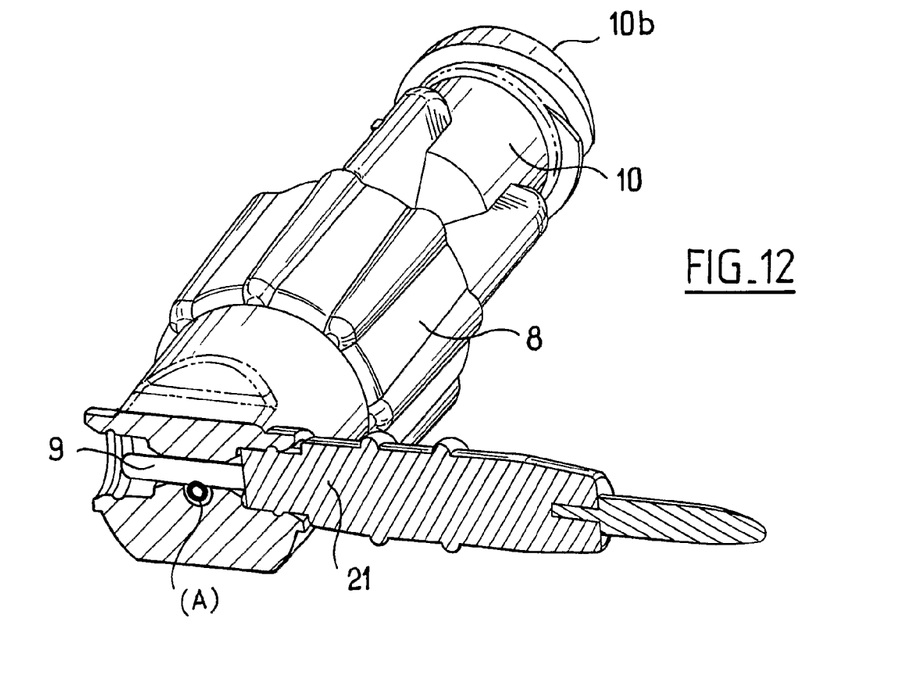
FIG. 12 is a cross-section view of the base according to the alternative embodiment, at the electric connection.

The base comprises a tubular body (10), onto an end (10a) of which a nut (11) may be screwed so as to provide compression of an elastomeric sleeve (12), housed in the nut (embodiment of FIGS. 1-7) or in the tubular body (embodiment of FIGS. 8-12) and crossed by the catheter tube when the latter is introduced into the base; the other end (10b) of the tubular body includes a conical inlet (Luer conicity) passage for connecting the end piece of a solution-supplying device.

The nut and the sleeve cooperate in order to provide holding of the catheter in the base by lateral compression of the catheter.

In order to provide the electric connection, the base has a side hole (13) which is formed in the tubular body (embodiment of FIGS. 1-7) or in the nut (embodiment of FIGS. 8-12), for letting through a wire (14) or a plug (15) of an electric conductor (9) right up to the contact with the catheter tube.

In order to provide passage of the current according to the embodiment of FIGS. 1-7, a split and elastic metal tube (5) with one (or more) spring tabs (6) cut out in the tube and S-shaped, so as to be jutting out inside and outside the tube, is slipped onto the proximal end of the catheter tube. In this way, this tube may be facing the side hole (13) of the base. The catheter tube is pushed into the base until it abuts in the base. The tab(s) of the metal tube is/are supported on the proximal ring of the conducting layer in order to provide the electric contact. The catheter tube is blocked in the base by the compression sleeve (7) tightened by the nut.

The exposed electric wire (9) covered with a metal ring (11) is pushed into the side hole (13) and blocked. It compresses the tab on the outside and provides the passage of the current of the wire towards the proximal ring.

The ring may be forcibly pushed, or force-fitted and held by a screw-nut type system, the side hole of the base is then threaded on the outside and the ring is equipped with a screwable nut.

In the latter case, the wire may be dismantled.

In an alternative embodiment (FIGS. 8-12) electric transmission between the catheter and the electric power supply wire is obtained by a direct side contact between the conductive cladding of the catheter and the wire.

In an example according to this alternative, the proximal end of the catheter tube, which includes the outer conducting layer (A) but which is without the insulating layer, is freely and directly slipped into the base (10), right up to an abutment (19) and is blocked in position by a compressing sleeve (12) which is compressed by screwing a nut (8) onto the base, as previously.

The base includes a chamber (15) for receiving the sleeve terminated at its proximal end by a conical wall (16).

An anti-friction ring (17) may be placed into the base if there is too much friction between the nut and the sleeve during the compression screwing, so as to prevent the sleeve from twisting.

De facto, the base, the sleeve and the nut are pre-assembled (without any tightening) before introducing the catheter into the base.

If the base is transparent, the abutment of the catheter may be observed in the base.

The whole length of catheter introduced into the base is conductive. Beyond the base, the catheter is covered with electrically insulating cladding (B).

The nut is screwed in, in order to compress the sleeve and to block the catheter. The seal is obtained in the proximal portion of the base. The liquid pushed into the female Luer of the base comes right up into the catheter. If liquid is introduced between the catheter and the sidewall of the lumen (20), it is collected in a very small chamber (18), the seal of which is provided by the sleeve (12) compressed between the cone (16) of the chamber (15) and against the catheter.

After blocking the nut, the conductive plug (19) of the electric line is introduced, which will bring the electric current into a side hole (13) of the nut. The plug will come into contact with the outer conductive surface of the catheter. Clipping of the base (21) of this plug into the hole of the nut is possible.

In order to achieve the conducting line, a silver-based conducting ink is preferably used. Silver is an ideal material for its conductivity (its resistivity is very low) and its flexibility (it follows without difficulty the curvatures of the tube). As an indication, with a thickness of 15-20 μm over the whole surface of the catheter tube ($\phi$ 0.40×0.83 mm), a resistance of about 8 ohms is obtained. Now considering the passage of a few mA in neurostimulation, it is better to have a resistance as low as possible.

This ink may be a mixture of solvent and very fine silver powder for very good electric conductivity.

The application may be achieved by screen printing, pad printing, or even with an ink jet. These application methods are non-limiting.

The invention is not limited to the embodiments which have been described.

The invention claimed is:

1. A neurostimulation catheter formed by a flexible tube of a non-electrically conducting material, a distal end of which is rounded, said neurostimulation catheter comprising an electric conductor which extends over a length of the flexible tube in order to conduct an electric stimulation current from one end of said flexible tube to the other end of said flexible tube, said electric conductor being formed by at least one layer of an electrically conducting material applied on an outer face of a sidewall of the flexible tube and a non-conducting cladding applied onto the electric conductor, said electric conductor forming at a distal end of the flexible tube a distal ring which fits a rounded shape of the distal end of the flexible tube and which is not covered by the non-conducting cladding so as to form a neurostimulation contact, and said electric conductor forming at a proximal end of the flexible tube a proximal ring which is not covered by the non-conducting cladding in order to achieve electric connection, and said non-conducting cladding extending along the whole length of the electric conductor between said distal ring and said proximal ring, said neurostimulation catheter further comprising a split conducting tube slipped onto the proximal end of the flexible tube in order to achieve electric connection with the proximal ring, wherein a wall of the split conducting tube is cut out longitudinally in order to form at least one elastic tab intended for providing electric contact between the proximal ring of the conducting layer and an electric wire maintained in contact with the tab.

2. The catheter according to claim 1, wherein said electric conductor forms a conducting line with calibrated width and thickness.

3. The catheter according to claim 1 or 2, wherein said electric conductor comprises an ink containing silver.

4. The catheter according to claim 1 or 2, wherein said electric conductor comprises a mixture of solvent and silver powder.

5. The catheter according to claim 1, wherein said electric conductor has been applied by screen printing, by pad printing, or by ink jet.

6. A neurostimulation catheter formed by a flexible tube of a non-electrically conducting material, a distal end of which is rounded, said neurostimulation catheter comprising an electric conductor which extends over a length of the flexible tube in order to conduct an electric stimulation current from one end of the flexible tube to the other end of the flexible tube, said electric conductor being formed by at least one layer of an electrically conducting material applied on an outer face of a sidewall of the flexible tube, and a non-conducting cladding applied onto the electric conductor, said electric conductor forming at a distal end of the flexible tube a distal ring which fits a rounded shape of the distal end of the flexible tube and which is not covered by the non-conducting cladding so as to form a neurostimulation contact, and said electric conductor forming at a proximal end of the flexible tube a proximal ring which is not covered by the non-conducting cladding in order to achieve electric connection, and said non-conducting cladding extending along the whole length of the electric conductor between said distal ring and said proximal ring, the neurostimulation catheter further including a proximal base equipped with means for maintaining the catheter in the proximal base and with means for providing electric connection between an electric power supply conductor and the electric conductor of the neurostimulation catheter, and being capable of connecting the neurostimulation catheter with a device supplying a solution, wherein the proximal base of said neurostimulation catheter includes a tubular body onto one end of which a nut may be screwed, in order to provide compression of an elastomeric sleeve housed in the nut or in the tubular body and crossed by the flexible tube when said flexible tube is introduced into the proximal base through said end of the tubular body, another end of the tubular body including a conical inlet passage for connecting an end piece of a solution supplying device.

7. The catheter according to claim 6, wherein said elastomeric sleeve is housed in the nut.

8. The catheter according to claim 6, wherein said elastomeric sleeve is housed in the body of the proximal base.

9. The catheter according to claim 6, wherein said means for providing an electric connection between the electric power supply conductor and the electric conductor comprise a side hole formed in the proximal base.

10. The catheter according to claim 9, wherein the side hole is formed in the tubular body of the proximal base.

11. The catheter according to claim 9, wherein the side hole is formed in the nut of the proximal base.

12. The catheter according to claim 6, wherein said electric conductor forms a conducting line with calibrated width and thickness.

13. The catheter according to claim 6, wherein said electric conductor comprises an ink containing silver.

14. The catheter according to claim 6, wherein said electric conductor comprises a mixture of solvent and silver powder.

15. The catheter according to claim 6, wherein said electric conductor has been applied by screen printing, by pad printing, or by ink jet.

16. The catheter according to claim 6, further comprising a split conducting tube slipped onto the proximal end of the flexible tube in order to achieve electric connection with the proximal ring.

17. The catheter according to claim 16, wherein a wall of the split conducting tube is cut out longitudinally in order to form at least one elastic tab intended for providing electric contact between the proximal ring of the conducting layer and an electric wire maintained in contact with the tab.

18. A neurostimulation catheter formed by a flexible tube of a non-electrically conducting material, a distal end of which is rounded, said neurostimulation catheter comprising an electric conductor which extends over a length of the flexible tube in order to conduct an electric stimulation current from one end of the flexible tube to the other end of the flexible tube, said electric conductor being formed by at least one layer of an electrically conducting material applied on an outer face of a sidewall of the flexible tube, and a non-conducting cladding applied onto the electric conductor, said electric conductor forming at a distal end of the flexible tube a distal ring which fits a rounded shape of the distal end of the flexible tube and which is not covered by the non-conducting cladding so as to form a neurostimulation contact, and said electric conductor forming at a proximal end of the flexible tube a proximal ring which is not covered by the non-conducting cladding in order to achieve electric connection, and said non-conducting cladding extending along the whole length of the electric conductor between said distal ring and said proximal ring, the neurostimulation catheter further including a proximal base equipped with means for maintaining the catheter in the proximal base and with means for providing electric connection between an electric power supply conductor and the electric conductor of the neurostimulation catheter, and being capable of connecting the neurostimulation catheter with a device supplying a solution, wherein said means for providing an electric connection between the electric power supply conductor and the electric conductor comprise a side hole formed in a nut of the proximal base.

* * * * *